(12) United States Patent
Cotticelli et al.

(10) Patent No.: US 7,411,077 B2
(45) Date of Patent: Aug. 12, 2008

(54) PROCESS FOR THE PREPARATION OF A CYANO-ISOBENZOFURAN

(75) Inventors: Giovanni Cotticelli, Milan (IT); Leone Dall'Asta, Milan (IT); Gianluca Di Lernia, Milan (IT)

(73) Assignee: Adorken Technology SpA, Costa Volpino (Bergamo) (IT)

( * ) Notice: Subject to any disclaimer, the term of this patent is extended or adjusted under 35 U.S.C. 154(b) by 81 days.

(21) Appl. No.: 10/549,062

(22) PCT Filed: Mar. 9, 2004

(86) PCT No.: PCT/EP2004/002522

§ 371 (c)(1),
(2), (4) Date: Feb. 27, 2006

(87) PCT Pub. No.: WO2004/809988

PCT Pub. Date: Sep. 23, 2004

(65) Prior Publication Data

US 2006/0183925 A1    Aug. 17, 2006

(30) Foreign Application Priority Data

Mar. 13, 2003  (IT) .......................... MI2003A0479

(51) Int. Cl.
*C07D 307/87* (2006.01)
*C07D 307/00* (2006.01)

(52) U.S. Cl. ...................................... 549/467; 549/307
(58) Field of Classification Search ................ 549/467, 549/307

See application file for complete search history.

(56) References Cited

U.S. PATENT DOCUMENTS 4,136,193 A  *  1/1979  Bogeso et al. ............... 514/469

FOREIGN PATENT DOCUMENTS

| EP | 1 095 926 A2 | 8/2000 |
| EP | 1 125 907 A2 | 8/2001 |
| WO | WO 98/19511 | * 11/1997 |
| WO | WO 98/19511 | * 5/1998 |

* cited by examiner

*Primary Examiner*—D. Margaret Seaman
*Assistant Examiner*—Nizal S Chandrakumar
(74) *Attorney, Agent, or Firm*—Perkins Coie LLP

(57) ABSTRACT

A process for the preparation of citalopram and the pharmaceutically acceptable salts therof is disclosed by reacting 5-cyanophthalide with a 4-fluorophenyl magnesium halide, reducing the 3-hydroxymethyl-4-(4-fluorobenzoyl)benzonitrile with an agent reducing ketones to alcohols, submitting the thus-obtained 3-hydroxymethyl-4-[(4-fluorophenyl)hydroxymethyl)benzonitrile to a cyclization reaction to give 1-(4-fluorophenyl)-1,3-dihydro-5-isobenzofurancarbonitrile without 1,1-bis(4-fluorophenyl)-1,3-dihydro-5-isobenzofurancarbonitrile and treating 1,1-bis(4 fluorophenyl)-1,3-dihydro-5-isobenzofurancarbonitrile with a 3-(dimetylamino) propyl halide in the presence of a base.

12 Claims, 3 Drawing Sheets

NMR CHARACTERIZATION

| $^1$H-NMR (DMSO-d6) | | | |
|---|---|---|---|
| δ (p.p.m.) | MULTIPLICITY | N° H | ASSIGNMENT |
| 8,01 | s | 1 | H8 |
| 7,62 - 7,60 | d | 1 | H7 |
| 7,19 - 7,17 | m | 8 | H1 e H2 |
| 6,96 | s | 1 | H3 |
| 6,74 - 6,72 | d | 1 | H6 |
| 5,29 - 5,26 | t | 1 | H5 |
| 4,39 - 4,38 | s | 2 | H4 |

| $^{13}$C-NMR (DMSO-d6) | | |
|---|---|---|
| δ (p.p.m.) | MULTIPLICITY | ASSIGNMENT |
| 163 - 161 | d | C1 |
| 149 | s | C8 |
| 145 | s | C6 |
| 143 | s | C4 |
| 131 - 130 | m | C9+C3+C11+C12 |
| 119 | s | C13 |
| 115,7 - 115,5 | d | C2 |
| 111 | s | C10 |
| 81 | s | C5 |
| 61 | s | C7 |

NMR CHARACTERIZATION

| $^1$H-NMR (DMSO-d6) | | | |
|---|---|---|---|
| δ (p.p.m.) | MULTIPLICITY | N° H | ASSIGNMENT |
| 7,89 | s | 1 | H4 |
| 7,82 - 7,81 | d | 1 | H5 |
| 7,61 - 7,59 | d | 1 | H6 |
| 7,32 – 7,15 | m | 8 | H1 + H2 |
| 5,16 | s | 1 | H3 |

| $^{13}$C-NMR (DMSO-d6) | | |
|---|---|---|
| δ (p.p.m.) | MULTIPLICITY | ASSIGNMENT |
| 163 – 161 | d | C1 |
| 149 | s | C8 |
| 141 - 140 | 2s | C7 + C4 |
| 133 | s | C10 |
| 129,9 – 129,8 | d | C3 |
| 125 - 127 | 2s | C12 + C9 |
| 119 | s | C13 |
| 116,1 – 115,9 | d | C2 |
| 111 | s | C11 |
| 92 | s | C5 |
| 71 | s | C6 |

NMR CHARACTERIZATION

| $^1$H-NMR (DMSO-d6) | | | |
|---|---|---|---|
| δ (p.p.m.) | MULTIPLICITY | N° H | ASSIGNMENT |
| 7,96 | s | 1 | H5 |
| 7,81 - 7,78 | d | 1 | H6 |
| 7,51 - 7,26 | m | 5 | H1 + H2 + H7 |
| 6,34 | s | 1 | H3 |
| 5,44 - 5,41 | d | 1 | H4 |
| 5,26 - 5,23 | d | 1 | H4' |

| $^{13}$C-NMR (DMSO-d6) | | |
|---|---|---|
| δ (p.p.m.) | MULTIPLICITY | ASSIGNMENT |
| 163 – 161 | d | C1 |
| 147 | s | C8 |
| 141 | s | C4 |
| 138 | s | C7 |
| 133 | s | C10 |
| 129,54 – 129,46 | d | C3 |
| 126 – 123 | 2s | C9 + C12 |
| 119 | s | C13 |
| 116,3 – 116,1 | d | C2 |
| 111 | s | C11 |
| 85 | s | C5 |
| 73 | s | C6 |

PROCESS FOR THE PREPARATION OF A CYANO-ISOBENZOFURAN

This application claims the benefit of PCT Application no. PCT/EP2004/002522, filed on Mar. 9, 2004, which in turn claims priority to Italy patent application no. MI2003 A 000479, filed on Mar. 13, 2003, both of which are incorporated herein in their entirety by reference.

The present invention concerns a process for the preparation, with a sole series of reactions, of pure 1-(4-fluorophenyl)-1,3-dihydro-5-isobenzofurancarbonitrile and for its conversion into the 1-[(3-(dimethylamino)propyl]-1-(4-fluorophenyl)-1,3-dihydro-5-isobenzofurancarbonitrile and its pharmaceutical acceptable salt.

Said cyano-isobenzofuran, 1-[(3-(dimethylamino)propyl]-1-(4-fluorophenyl)-1,3-dihydro-5-isobenzo furancarbonitrile, represented by the formula A

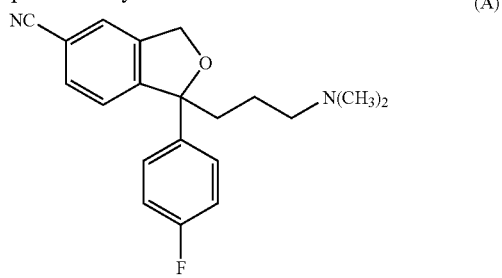

(A)

known with its International Non-proprietary Name "citalopram" is an active principle of drugs used, in form of its hydrobromide, for the preparation of pharmaceutical compositions for the treatment of depression.

Citalopram was described for the first time in the Belgian patent 850,401 (corresponding to U.S. Pat. No. 4,136,193) and many methods for its preparation have been patented.

Document U.S. Pat. No. 4,136,193 discloses a family of compounds of formula A'

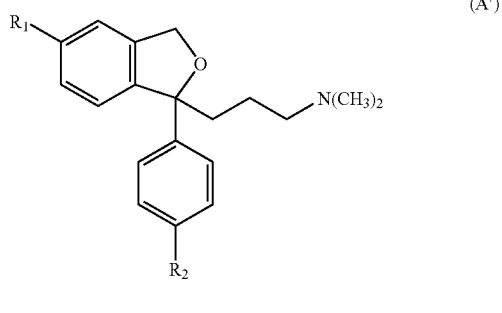

(A')

wherein $R_1$ and $R_2$ represent each a halogen, a trifluoromethyl group, a cyano group or a group R—CO— in which R is $C_1$-$C_4$ alkyl. According to said document, the compounds of formula A' may be prepared by reaction of a compound of formula B'

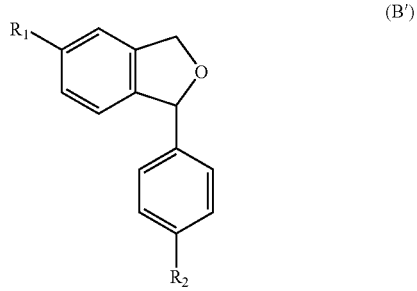

(B')

wherein $R_1$ and $R_2$ are as defined above, with a 3-(dimethylamino)propyl halide in the presence of a base. The same document does not say how the compounds of formula B' in which $R_1$ is cyano and $R_2$ is fluoro are prepared, but in two examples it provides the preparation of a compound of formula B', in which $R_1$ is bromo and $R_2$ is fluoro, by reaction of 5-bromophthalide with 4-fluorophenyl magnesium bromide, reduction of 3-hydroxymethyl-4-(4-fluorobenzoyl)bromobenzene thus obtained with lithium aluminium hydride and cyclization of the diol thus obtained of formula C'

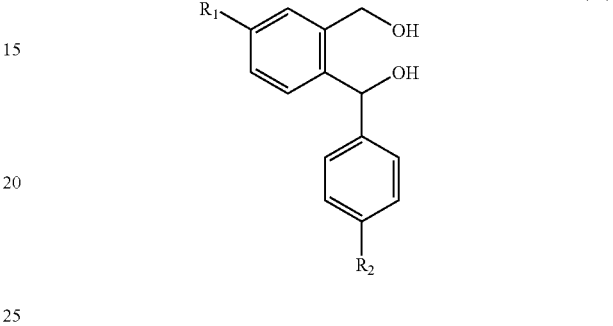

(C')

wherein $R_1$ is bromo and $R_2$ is fluoro, with 60% phosphoric acid. From this document an ordinary expert infers that the method for the preparation of the compounds of formula A' is of general character and that the reaction with 4-fluorophenyl magnesium bromide may be performed on the 5-cyanophthalide too.

In fact, EP 171,943 discloses a method of synthesis which uses two Grignard reactions starting from 5-cyanophthalide, the first one being with 4-flourophenyl magnesium bromide and the second, on the magnesium derivative obtained, with 3-(dimethylamino)propyl magnesium chloride to obtain a diol, precursor of citalopram, of formula D

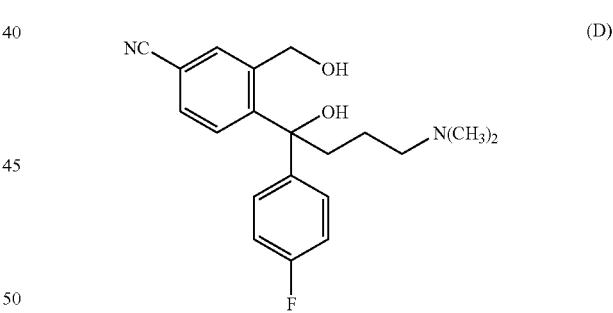

(D)

which is cyclized to citalopram.

Analogously, the document WO 98/19511 (corresponding to U.S. Pat. No. 6,291,689) discloses a process wherein the 3-hydroxymethyl-4-(4-fluorobenzoyl)benzonitrile is reduced with sodium borohydride to obtain the diol of formula C', wherein $R_1$ is cyano and $R_2$ is fluoro, which is cyclized to 1-(4-fluorophenyl)-1,3-dihydro-5-isobenzofuran carbonitrile in its turn converted to citalopram by reaction with 3-(dimethylamino)propyl chloride in the presence of a base. According to this document, the process may be carried out by isolating the intermediates or without isolating them, but said document does not give any information on how to carry out the process in a sole operation.

Furthermore, the process described in WO 98/19511, which substantially overlaps that disclosed in the preceding documents BE 850,401 and U.S. Pat. No. 4,136,193, provides 1-(4-fluorophenyl)-1,3-dihydro-5-isobenzofurancarbonitrile (compound of formula B' in which $R_1$=CN and $R_2$=F) in a yield of 29% only.

It has been hypothesized and experimentally demonstrated that the reaction of 4-fluorophenyl magnesium bromide with 5-cyanophthalide leads to a mixture in which, beside the desired 3-hydroxymethyl-4-(4-fluorobenzoyl)benzonitrile, the 3-hydroxymethyl-4-[bis(4-fluorophenyl)hydroxymethyl]benzonitrile is present in not negligible amounts. In the subsequent cyclization this by-product, which remains unaltered during the reduction, for example with $LiAlH_4$ or $NaBH_4$, gives the 1,1-bis(4-fluorophenyl)-1,3-dihydro-5-isobenzofurancarbonitrile which, being difficulty separable from the intermediate 1-(4-fluorophenyl)-1,3-dihydro-5-isobenzofurancarbonitrile, involves noteworthy problems in the synthesis of the final citalopram. The confirmation of the formation of the above-mentioned by-products was possible by treatment of 5-cyanophthalide with an excess of 4-fluorophenyl magnesium bromide which, by favouring the formation of the 3-hydroxymethyl-4-[bis(4-fluorophenyl)hydroxymethyl]benzonitrile, allowed the isolation and the characterization of this by-product. The same principle has been applied to the preparation of 1,1-bis(4-fluorophenyl)-1,3-dihydro-5-isobenzofurancarbonitrile which has thus been isolated and characterized. Through the study of the solubility of 1,1-bis(4-fluorophenyl)-1,3-dihydro-5-isobenzofurancarbonitrile and of the 1-(4-fluorophenyl)-1,3-dihydro-5-isobenzofurancarbonitrile, it was possible to succeed in the separation of the two products in the course of the synthesis of citalopram starting from 5-cyanophthalide.

In particular, thanks to the identification of the by-products, it has been found that, by operating according to Example 3 of BE 850,401 (U.S. Pat. No. 4,036,193), starting from 5-cyanophthalide, after the reaction with 4-fluorophenyl magnesium halide, the subsequent reduction to diol (C)

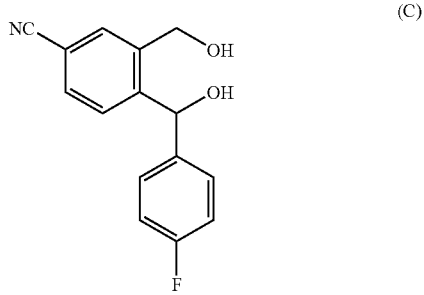

and the cyclization to 1-(4-fluorophenyl)-1,3-dihydro-5-isobenzofurancarbonitrile (B)

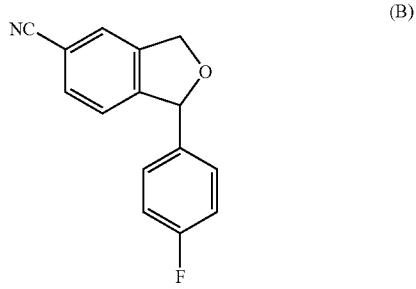

it is possible to isolate the mixture containing the 1-(4-fluorophenyl)-1,3-dihydro-5-isobenzofurancarbonitrile and the 1,1-bis-(4-fluorophenyl)-1,3-dihydro-5-isobenzofuran carbonitrile and to treat said mixture with a solvent capable of dissolving the 1,1-bis-(4-fluorophenyl)-1,3-dihydro-5-isobenzofurancarbonitrile under condition in which 1-(4-fluorophenyl)-1,3-dihydro-5-isobenzofurancarbonitrile is practically insoluble, for example with isopropanol or with methyl-t-butylether. Under these conditions, the pure 1-(4-fluorophenyl)-1,3-dihydro-5-isobenzofurancarbonitrile (B) is recovered in very high yields while the by-product 1,1-bis-(4-fluorophenyl)-1,3-dihydro-5-isobenzofurancarbonitrile remains in solution and is thus eliminated.

The reaction sequence takes place according to Scheme 1 below, wherein a preferred embodiment is illustrated.

From 1-(4-fluorophenyl)-1,3-dihydro-5-isobenzofurancarbonitrile thus obtained, by reaction with a 3-(dimethylamino)propyl halide in the presence of a condensing agent such as an alkaline metal, for example sodium amide or potassium amide, butyl lithium, phenyl lithium, sodium hydride and the like, as described in BE 850,401 (U.S. Pat. No. 4,136,193), it is possible to obtain the citalopram in a high degree of purity in form of free base or of one of its non toxic acid addition salts.

The expressions "pure citalopram" and "citalopram at high purity degree" indicate citalopram or a pharmaceutically acceptable salt thereof, in particular the hydrobromide, in which the 1,1-bis(4-fluorophenyl)-1,3-dihydro-5-isobenzofurancarbonitrile is not detectable in the NMR spectrum obtained with a Bruker AMX 400 MHz apparatus.

The terms "soluble" and "insoluble" and the expression "capable of dissolving" indicate a solubility degree of the above compounds which allows an average skilled in the art to dissolve a product under normal conditions, namely at a reasonable concentration and temperature or to consider that, at said reasonable concentration and temperature said product does not dissolve, talking into account that in the case of 1-(4-fluorophenyl)-1,3-dihydro-5-isobenzofurancarbonitrile and of 1,1'-bis(4-fluorophenyl)-1,3-dihydro-5-isobenzofurancarbonitrile it is a matter of evaluating a difference of solubility between the two compounds. In an indicative but not limiting manner it may be considered that a solvent is suitable to the separation of the two compounds if, in said solvent, the 1,1'-bis(4-fluorophenyl)-1,3-dihydro-5-isobenzofurancarbonitrile is "very soluble", "soluble" or "fairly soluble" according to the criteria of the European Pharmacopea or of the United States Pharmacopea (USP) while, in the same solvent, the 1-(4-fluorophenyl)-1,3-dihydro-5-isobenzofurancarbonitrile is "very slightly soluble" or "practically insoluble".

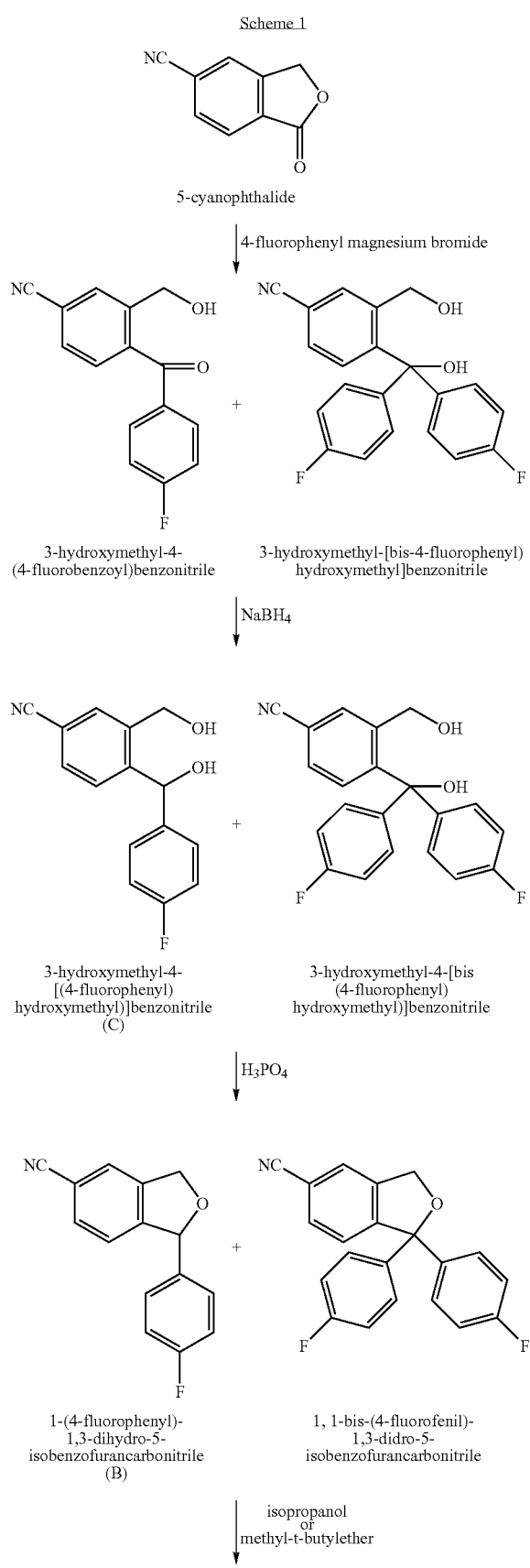

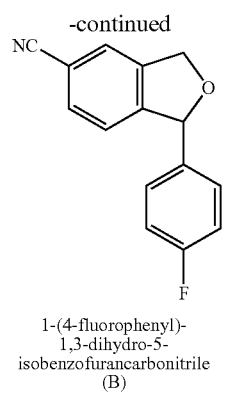

1-(4-fluorophenyl)-
1,3-dihydro-5-
isobenzofurancarbonitrile
(B)

Figure 3:
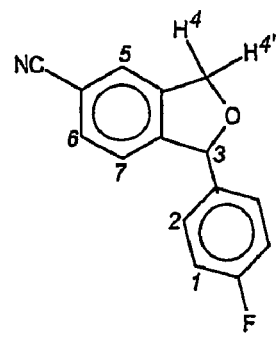
Figure 3:
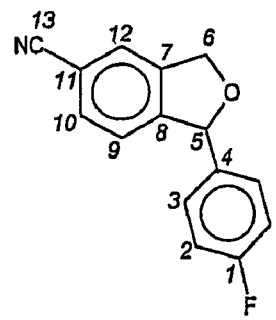

FIG. 3 illustrates the characteristics of the pure 1-(4-fluorophenyl)-1,3-dihydro-5-isobenzofurancarbonitrile in the $^1$H-NMR and $^{13}$C-NMR spectra obtained with a Bruker AMX 400 MHz apparatus.

Thus, it is an object of the present invention to provide a process for the preparation of 1-(4-fluorophenyl)-1,3-dihydro-5-isobenzofurancarbonitrile which comprises:

(a) reacting 5-cyanophthalide with a 4-fluorophenyl magnesium halide;

(b) treating the mixture thus obtained, containing the 3-hydroxymethyl-4-(4-fluoro-benzoyl)benzonitrile and the 3-hydroxymethyl-4-[bis-(4-fluorophenyl)hydroxymethyl]benzonitrile; with an agent reducing ketones to alcohols;

(c) submitting the mixture thus obtained, containing the 3-hydroxymethyl-4-[(4-fluorophenyl)hydroxymethyl]benzonitrile (C) and the 3-hydroxymethyl-4-[bis-(4-fluoro-phenyl)hydroxymethyl]benzonitrile, to a cyclization reaction and isolating a mixture containing the 1-(4-fluorophenyl)-1,3-dihydro-5-isobenzofurancarbonitrile and the 1-(4-fluorophenyl)-1,3-dihydro-5-isobenzofurancarbonitrile (B) and the 1,1-bis(4-fluorophenyl)-1,3-dihydro-5-isobenzofurancarbonitrile;

(d) treating the mixture thus obtained with a solvent capable of dissolving the 1,1-bis(4-fluorophenyl)-1,3-dihydro-5-isobenzofurancarbonitrile and in which the 1-(4-fluorophenyl)-1,3-dihydro-5-isobenzofurancarbonitrile (B) is insoluble and recovering the pure 1-(4-fluorophenyl)-1,3-dihydro-5-isobenzofurancarbonitrile (B).

Steps (a), (b) and (c) are carried out without isolating the intermediate compounds according to known literature methods, for example according to the method cited in U.S. Pat. No. 4,136,193 and specifically described, starting from 5-bromophthalide, in examples 1 and 3 of said document.

In particular, step (a), consisting of the treatment of 5-cyanophthalide with a 4-fluorophenylmagnesium halide, occurs according to a classical Grignard reaction procedure, for example under the conditions described in Example 1 of U.S. Pat. No. 4,136,193 for the 5-bromophthalide, by treating 1.05-1.35 equivalents of a Grignard solution, titred at 15-20%, said solution being prepared from p-fluorobromobenzene and magnesium turnings in an ether, for example in tetrahydrofuran, with 5-cyanophthalide and by adding said Grignard reagent in the amount capable of consuming practically the whole starting 5-cyanophthalide. In practice, the operator controls the course of the reaction by HPLC [column: Develosil C18 4.6×250 mm, 5μ; DETECTOR: UV 240 nm; FLOW: 1.5 ml/min; GRADIENT: A: aqueous $NH_4H_2PO_4+H_3PO_4$ at pH=2.85/B: $CH_3CN/H_2O$=9/1 (v/v)] and stops it when 2-3% of unreacted 5-cyanophthalide remains. The product thus obtained is directly submitted to the next step (b) consinsting of a reduction with an agent reducing ketones to alcohols for example with $NaBH_4$, or with $LiAlH_4$ as described in Example 3 of U.S. Pat. No. 4,136,193, to obtain the corresponding 3-hydroxymethyl-4-[(4-fluorophenyl)hydroxymethyl]benzonitrile.

According to a preferred embodiment, which allows the large scale preparation under conditions of safety, the reduction is carried out with an aqueous solution of $NaBH_4$ and sodium hydroxide. Said aqueous solution is added at a temperature not higher than 15° C. and the reaction is complete at the end of the addition. Thus, it is sufficient to eliminate the aqueous phase, to evaporate the organic solvent and to submit the residue to the subsequent step (c).

Step (c), consisting of the diol cyclization, is conducted by treating the material obtained at the end of step (b) with 60% phosphoric acid as described in Example 1 of U.S. Pat. No. 4,136,193 for the corresponding 3-hydroxymethyl-4-[(4-fluorophenyl)hydroxymethyl]-bromobenzene.

According to a preferred embodiment, the method described in U.S. Pat. No. 4,136,193 is rendered easier by dissolving the material obtained at the end of step (b) in an organic solvent, preferably ethyl acetate or tetrahydrofuran, and by carrying out the reaction with 60% phosphoric acid in a biphasic system, thus avoiding the formation of waxy residues which are difficult to treat. In practice, the residue obtained according to the preferred mode of conducting step (b) is dissolved in ethyl acetate and, after the addition of 60% phosphoric acid, the reaction is carried out in a biphasic, for example water/ethyl acetate, system.

In step (d), the crude material thus obtained, containing the 1-(4-fluorophenyl)-1,3-dihydro-5-isobenzofurancarbonitrile (B) and the 1,1-bis(4-fluorophenyl)-1,3-dihydro-5-isobenzofurancarbonitrile is treated with a solvent capable of dissolving the 1,1-bis(4-fluorophenyl)-1,3-dihydro-5-isobenzofurancarbonitrile under conditions in which the 1-(4-fluorophenyl)-1,3-dihydro-5-isobenzofurancarbonitrile (B) is practically insoluble, for example with isopropanol or with methyl-t-butylether.

According to a preferred embodiment, the process of the present invention is carried out "one-pot", i.e. without isolating the intermediate products, until a 1-(4-fluorophenyl)-1,3-dihydro-5-isobenzofurancarbonitrile practically devoid of 1,1-bis(4-fluorophenyl)-1,3-dihydro-5-isobenzofurancarbonitrile is obtained, said 1-(4-fluorophenyl)-1,3-dihydro-5-isobenzofurancarbonitrile being subsequently converted into citalopram. In practice, a Grignard solution is prepared by adding a solution of 4-fluorobromobenzene in tetrahydrofuran to magnesium turnings in the presence of traces of iodine at a temperature of about 70° C. and, after about 30 minutes, at the same temperature, the solution is added portionwise to a suspension of 5-cyanophthalide in tetrahydrofuran at 20-0° C., preferably at −10-0° C. At the end of the reaction, namely when less than 5% of the starting 5-cyanophthalide is present, the magnesium derivative is decomposed with water or, better, with an aqueous solution of ammonium chloride and the cold tetrahydrofuranic solution, containing the 3-hydroxymethyl-4-(4-fluorobenzoyl)benzonitrile and the 3-hydroxymethyl-4[bis(4-fluorophenyl)hydroxymethyl]benzonitrile, is treated with an aqueous solution of $NaBH_4$ and of NaOH.

The obtained mixture, containing the 3-hydroxymethyl-4-[(4-fluorophenyl)hydroxymethyl]benzonitrile (C) and the 3-hydroxymethyl-4-[bis(4-fluorophenyl)hydroxymethyl] benzonitrile, is extracted with ethyl acetate. The organic phase is concentrated, the residue is taken up with an organic solvent, preferably with ethyl acetate, and the solution is treated with 60% phosphoric acid and heated. At the end of the reaction, after separation of the phases, the organic phase, containing the 1-(4-fluorophenyl)-1,3-dihydro-5-isobenzofurancarbonitrile and the 1,1-bis-(4-fluorophenyl)-1,3-dihydro-5-isobenzofurancarbonitrile, is washed with water, decolorized with activated charcoal and concentrated under vacuum. The oily residue is treated with the selected solvent, preferably with isopropanol or with methyl-t-butylether, then the solvent is evaporated under vacuum. If needed, the operation of treatment with the solvent and of subsequent evaporation is repeated several times until, by taking up with the solvent, a crystalline suspension consisting of pure 1-(4-fluorophenyl)-1,3-dihydro-5-isobenzofurancarbonitrile (B) is obtained. This compound is isolated in a 70-75% yield, calculated in respect of the starting 5-cyanophthalide, by simple filtration. In general, the product thus obtained, having a purity higher than 98%, contains the 1,1-bis(4-fluorophenyl)-1,3-dihydro-5-isobenzofurancarbonitrile in a percent lower than 0.5%, thus allowing the subsequent preparation of a citalopram with a high degree of purity, or of pharmaceutically acceptable salt thereof, by treatment with a 3-(dimethylamino)propyl halide in the presence of a basic condensing agent. This mode of operating is illustrated, in a preferred aspect thereof, in Scheme 2 below.

The 1-(4-fluorophenyl)-1,3-dihydro-5-isobenzofurancarbonitrile containing the 1,1-bis(4-fluorophenyl)-1,3-dihydro-5-isobenzofurancarbonitrile in a percent lower than 0.5% is a new product which represents a further object of the present invention.

The pure 1-(4-fluorophenyl)-1,3-dihydro-5-isobenzofurancarbonitrile (B) obtained at the end of steps (a)-(d) above may be further made to react with a 3-(dimethylamino) propyl halide in the presence of a basic condensing agent to isolate citalopram at a high purity degree, or a pharmaceutically acceptable salt thereof, in yields which are higher than those obtained with any other known process using 5-cyanophthalide as starting material.

Thus, it is another object of the present invention to provide a process for the preparation of citalopram or of a pharmaceutically acceptable salt thereof, which comprises:

(a) reacting 5-cyanophthalide with a 4-fluorophenyl magnesium halide;

(b) treating the mixture thus obtained, containing the 3-hydroxymethyl-4-(4-fluoro benzoyl)benzonitrile and the 3-hydroxymethyl-4-[bis-(4-fluorophenyl)hydroxymethyl]benzonitrile with a reducing agent of ketones to alcohols;

(c) submitting the mixture thus obtained, containing the 3-hydroxymethyl-4-[(4-fluorophenyl)hydroxymethyl]benzonitrile (C) and the 3-hydroxymethyl-4-[bis-(4-fluorophenyl)hydroxymethyl]benzonitrile to a cyclization and isolating a mixture containing the 1-(4-fluorophenyl)-1,3-dihydro-5-isobenzofurancarbonitrile (B) and the 1,1-bis(4-fluorophenyl)-1,3-dihydro-5-isobenzofurancarbonitrile;

(d) treating the mixture thus obtained with a solvent capable of dissolving the 1,1-bis(4-fluorophenyl)-1,3-dihydro-5-isobenzofurancarbonitrile and in which the 1-(4-fluorophenyl)-1,3-dihydro-5-isobenzofurancarbonitrile (B) is insoluble and recovering the pure 1-(4-fluorophenyl)-1,3-dihydro-5-isobenzofurancarbonitrile (B);

(e) treating the pure 1-(4-fluorophenyl)-1,3-dihydro-5-isobenzofurancarbonitrile (B) with a 3-(dimetylamino)propyl halide in the presence of a basic condensing agent and isolating citalopram as free base or as a pharmaceutically acceptable salt thereof.

Steps (a)-(d) are carried out as described above and the pure 1-(4-fluorophenyl)-1,3-dihydro-5-isobenzofurancarbonitrile (B) obtained at the end of step (d) is submitted to the subsequent step (e).

In step (e), the chloride, the bromide or the iodide may indifferently be used as halide, the chloride being preferred.

As a condensing basic agent, anyone of the bases commonly used in the alkylation reactions, such as sodium amide, potassium amide, butyl lithium, phenyl lithium or sodium hydride may be employed.

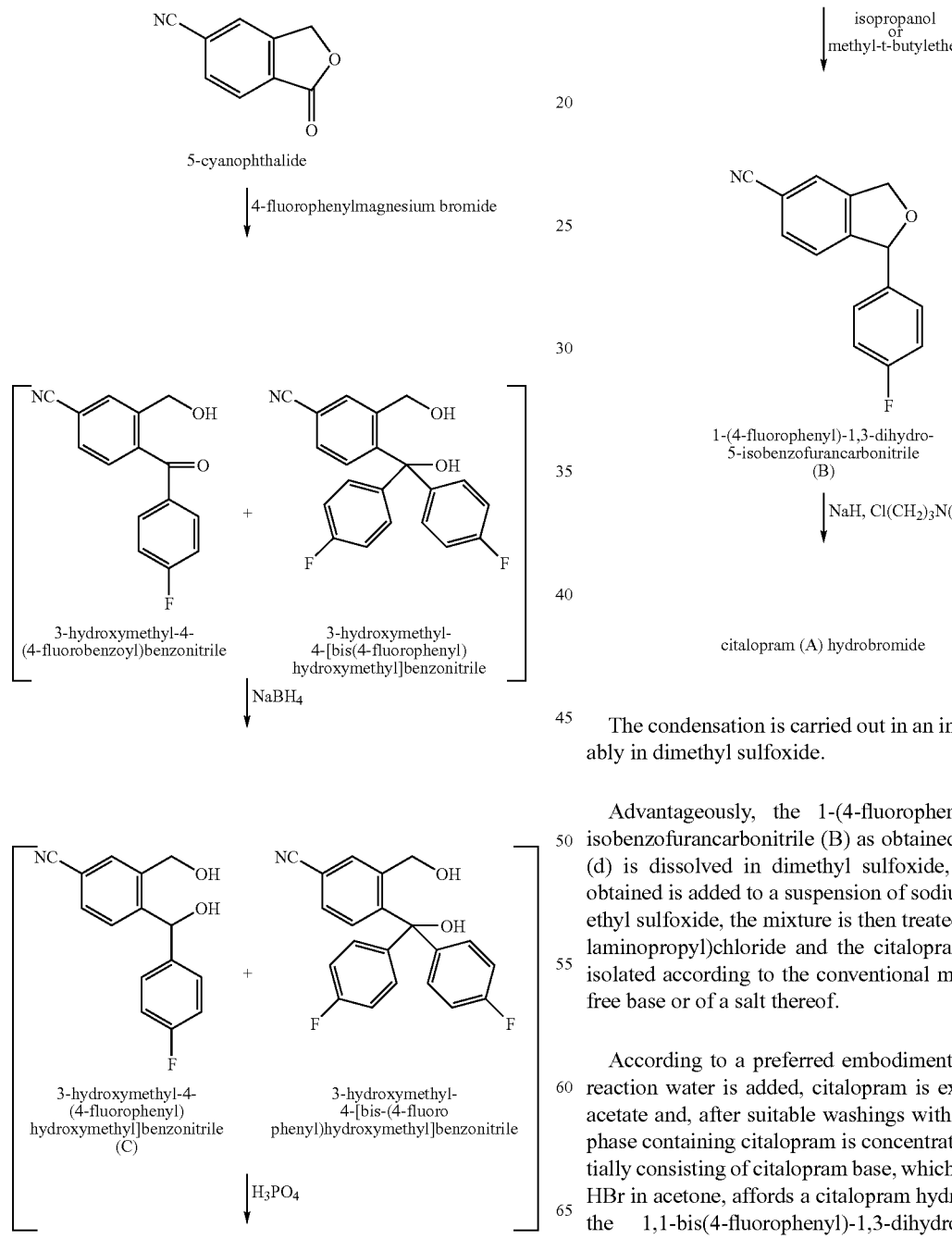

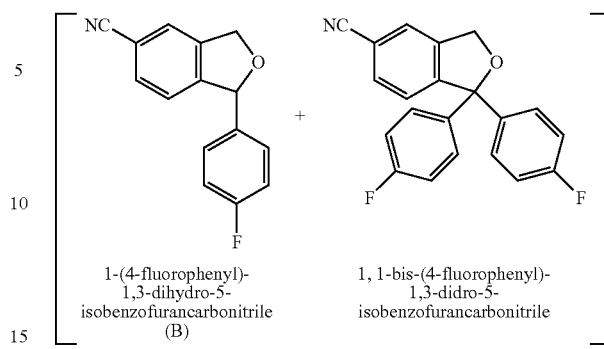

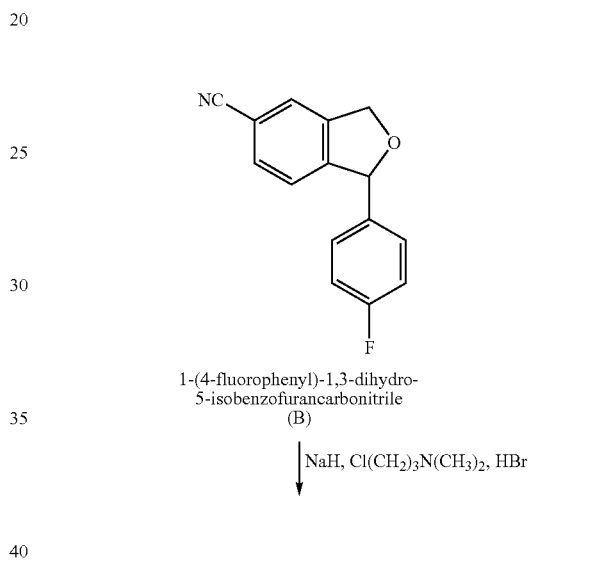

The condensation is carried out in an inert solvent, preferably in dimethyl sulfoxide.

Advantageously, the 1-(4-fluorophenyl)-1,3-dihydro-5-isobenzofurancarbonitrile (B) as obtained at the end of step (d) is dissolved in dimethyl sulfoxide, the solution thus obtained is added to a suspension of sodium hydride in dimethyl sulfoxide, the mixture is then treated with 3-(dimethylaminopropyl)chloride and the citalopram which forms is isolated according to the conventional methods, in form of free base or of a salt thereof.

According to a preferred embodiment, at the end of the reaction water is added, citalopram is extracted with ethyl acetate and, after suitable washings with water, the organic phase containing citalopram is concentrated to an oil, essentially consisting of citalopram base, which, by treatment with HBr in acetone, affords a citalopram hydrobromide wherein the 1,1-bis(4-fluorophenyl)-1,3-dihydro-5-isobenzofurancarbonitrile is not detectable in the NMR spectrum obtained with a Bruker AMX 400 MHz apparatus. The product thus obtained may be subsequently purified according to known methods, for example by repeated washings with cold water.

Thus, the process of the present invention allows the preparation of citalopram hydrobromide in yields much higher than those obtained by all of the methods employing the 5-cyanophthalide as starting material. Furthermore, by avoiding the use of intermediates containing a prcursor of the CN group, the process of the invention is easier to be carried out and affords a citalopram with high purity in very satisfactory yields.

In the preparations given hereinbelow the by-products that form in the synthesis starting from 5-cyanophthalide are isolated. They represent the reference standards for the control of the process of the invention.

The following examples illustrate the invention.

PREPARATION I

20% Solution of 4-fluorophenylmagnesium bromide in tetrahydrofuran

In a 4-l flask, under nitrogen flow and at room temperature, 53.5 g of magnesium turnings and 0.3 g of iodine particles are charged, then the mixture is heated to 70° C. and, in one hour, a solution of 369.5 g of 4-fluorobromobenzene in 1960 ml of tetrahydrofuran is dropped thereinto. At the end of addition the mixture is heated at reflux at 68-70° C. for 30 minutes, then the obtained solution is cooled to 25° C. There is obtained 2000 g of a 20% solution of 4-fluorophenylmagnesium bromide, to be stored in the dark and in nitrogen atmosphere.

PREPARATION II 3-hydroxymethyl-4[bis(4-fluorophenyl)hydroxymethyl]benzonitrile (a) Synthesis To a suspension of 20 g of 5-cyanophthalide in 150 ml of tetrahydrofuran, under nitrogen flow, at 25° C., 422.6 g of the 20% solution of 4-fluorophenylmagnesium bromide obtained in PREPARATION I are added and a rise in temperature of the mixture to about 35° C. is observed. The mixture is kept under stirring until, by a HPLC control [COLUMN: Develosil C18 4.6×250 mm, 5μ; DETECTOR: UV 240 nm; FLOW: 1.5 ml/min; GRADIENT: A: aq. $NH_4H_2PO_4+H_3PO_4$–pH=2.85/B: $CH_3CN/H_2O$=9/1 (v/v)], the disappearance of 5-cyanophthalide is observed. When the reaction is over, 200 ml of a 15% aqueous solution of ammonium chloride are added, maintaining the temperature not higher than 30° C., then the phases are separated and the organic one is concentrated under vacuum to obtain 52 g of a yellow oil, the raw 3-hydroxymethyl-4-[bis-(4-fluorophenyl)hydroxymethyl]benzonitrile, with a purity of 92.12%.

(b) Purification

In a 250-ml flask, 20 g of raw 3-hydroxymethyl-4-[bis(4-fluorophenyl)hydroxymethyl]benzonitrile obtained in the preceding synthesis and 100 ml of ethyl acetate are charged. The mixture is stirred until a solution is obtained, wherein 30 ml of silica gel 60 are added, then the solvent is evaporated under vacuum until a dry powder is obtained. Separately, a 5-cm diameter column is prepared with 300 ml of silica gel 60 (particles Ø 0.063-0.200 mm) for gravimetric column, using a mixture hexane/ethyl acetate 9/1 (v/v) as eluent. The product previously adsorbed on silica gel 60 is charged into the column prepared as described and is eluted with the mixture itself. The fractions containing the product are collected and concentrated under vacuum at 50° C. with Rotavapor® (the solution is getting foaming, so that during the concentration must be taken the due precautions). The oily residue obtained is treated with 100 ml dichloromethane and the solution is concentrated to give 11.6 g of 3-hydroxymethyl-4-[bis(4-fluorophenyl)hydroxymethyl]benzonitrile as white crystals with m.p.=66.4÷72.3° C. and purity (HPLC)=97.35%.

Figure 1:
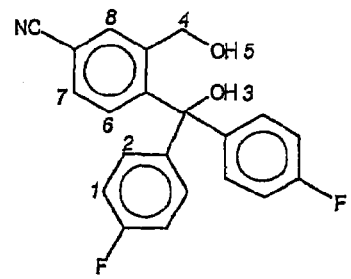
FIG. 1 illustrates the characteristics of the 3-hydroxymethyl-4-[bis(4-fluorophenyl)hydroxymethyl]benzonitrile in the $^1$H-NMR and $^{13}$C-NMR spectra obtained with a Bruker AMX 400 MHz apparatus.
Figure 1:
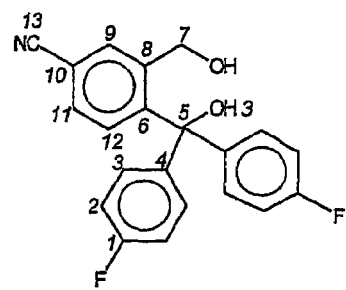

$^1$H-NMR and $^{13}$C-NMR product data are indicated in FIG. 1.

PREPARATION III 1,1-Bis(4-fluorophenyl)-1,3-dihydro-5-isobenzofurancarbonitrile (a) Synthesis In a 500-ml flask 22 g of raw 3-hydroxymethyl-4-[bis(4-fluorophenyl)hydroxy methyl]benzonitrile obtained in the preceeding step (a) of PREPARATION II and 100 ml of 60% $H_3PO_4$ are charged and the mixture is heated to 100° C. After 3½-hour stirring at the same temperature, the reaction is over: a control by HPLC [COLUMN: Develosil C18 4.6×250 mm, 5μ; DETECTOR: UV 240 nm; FLOW: 1.5 ml/min; GRADIENT: A: aq. $NH_4H_2PO_4+H_3PO_4$–pH=2.85/B: $CH_3CN/H_2O$=9/1 (v/v)] detects the presence of 0.2% starting material. The mixture is treated, after cooling at 25° C., with 100 ml of ethyl acetate and 125 g of water+ice, then it is stirred at 25° C. for 30 minutes. The phases are separated, the organic phase is collected and the aqueous one is extracted with 100 ml ethyl acetate. The aqueous phase is eliminated and the collected organic phases are washed with 150 ml of water. The separated organic phase is decolorized by treatment with 1 g activated charcoal. After 30-minute stirring at 25° C., the charcoal is eliminated by filtration through a Celite® layer and the filtrate is concentrated under vacuum at 50° C. until a orange-yellow oil is obtained. Thus 23 g of raw 1,1-bis(4-fluorophenyl)-1,3-dihydro-5-isobenzofurancarbonitrile are obtained, with a purity (HPLC)=88.6%.

(b) Purification

In a 1-l flask 21 g of raw 1,1-bis(4-fluorophenyl)-1,3-dihydro-5-isobenzofuran carbonitrile obtained in (a) and 400 ml of hexane are charged. The mixture is heated at reflux for 30 minutes, is cooled at 0° C. and is let under stirring for 2 hours at this temperature. The product is recovered as light yellow crystals by filtration and is washed with 20 ml of cold hexane. Thus 23 g of 1,1-bis(4-fluorophenyl)-1,3-dihydro-5-isobenzofurancarbonitrile are obtained, with m.p. 104.7-106.2° C. and purity=97.7%.

Figure 2:
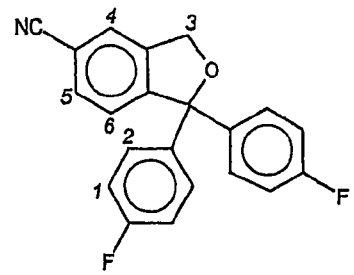
FIG. 2 illustrates the characteristics of the 1,1-bis(4-fluorophenyl)-1,3-dihydro-5-isobenzofurancarbonitrile in the $^1$H-NMR and $^{13}$C-NMR spectra obtained with a Bruker AMX 400 MHz apparatus.
Figure 2:
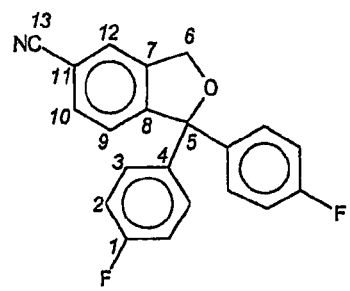

$^1$H-NMR and $^{13}$C-NMR product data are indicated in FIG. 2.

EXAMPLE 1

Pure 1-(4-fluorophenyl)-1,3-dihydro-5-isobenzofurancarbonitrile

To a suspension of 95 g of 5-cyanophthalide in 710 ml of tetrahydrofuran, previously cooled at –10° C., 384 g of a 20% solution of 4-fluorophenylmagnesium bromide in tetrahydrofuran obtained in PREPARATION I ("Grignard solution") are dropped thereinto, in two hours at a temperature not higher than –5° C., then, in the same conditions, in three times, 230 g, 115 g and 49 g of Grignard solution are dropped thereinto. When the reaction is over, 675 ml of a 15% aqueous solution of ammonium chloride are added in about one hour, maintaining the temperature lower than 0° C. The phases are separated, the aqueous one is extracted with 285 ml of tetrahydrofuran and the organic phase is collected.

The organic phase (950 ml), containing a theoretical quantity of 150 g of 3-hydroxymethyl-4-(4-fluorobenzoyl)benzonitrile, referred to the starting 5-cyanophthalide, and about 14-16% of 3-hydroxymethyl-4-[bis(4-fluorophenyl)hydroxymethyl]benzonitrile, is cooled at 0-5° C., under nitrogen atmosphere. A solution of 23.3 g of $NaBH_4$, 230 ml of water and 1 ml of 30% NaOH is added to the mixture dropwise, in 30 minutes and at a temperature not higher than 15° C. At the end of the addition a control by HPLC [COLUMN: Develosil C18 4.6×250 mm, 5μ; DETECTOR: UV 240 nm; FLOW: 1.5 ml/min; GRADIENT: A: aq. $NH_4H_2PO_4$+$H_3PO_4$-pH=2.85/B: $CH_3CN/H_2O$=9/1 (v/v)] detects the disappearance of 3-hydroxymethyl-4-(4-fluorobenzoyl)benzonitrile. The temperature is kept to 25° C., the aqueous phase is eliminated and tetrahydrofuran is evaporated under vacuum at 50° C. 100 ml of ethyl acetate are added to the residue and the solvent is evaporated under vacuum at 50° C., then other 350 ml of ethyl acetate are added. The phases are separated, the organic phase is collected and the aqueous phase is extracted with 230 ml of ethyl acetate. The phases are separated, the aqueous phase is discarded and the organic phases are collected obtaining 720 ml of a solution in ethyl acetate containing 150 g of 3-hydroxymethyl-4-[(4-fluorophenyl)hydroxymethyl]benzonitrile and the same quantity of 3-hydroxymethyl-4-[bis(4-fluorophenyl)hydroxymethyl]benzonitrile contained into the starting solution.

To this solution, 930 ml of 60% $H_3PO_4$ are added at 25° C. and the biphasic mixture water/ethyl acetate (81-82° C.) is heated at reflux for 2 hours. A control by HPLC (see above) shows the disappearance of 3-hydroxymethyl-4-[(4-fluorophenyl)hydroxymethyl]benzonitrile and of 3-hydroxymethyl-4-[bis(4-fluorophenyl)hydroxymethyl]benzonitrile contained in the starting solution. In the mixture thus obtained, containing the 1-(4-fluorophenyl)-1,3-dihydro-5-isobenzofurancarbonitrile and about 14-16% of 1,1-bis(4-fluorophenyl)-1,3-dihydro-5-isobenzofurancarbonitrile, 750 ml of water are dropped thereinto, then the phases are separated. The organic phase is collected and the aqueous one is extracted with 600 ml of ethyl acetate. After separation of the phases, the organic phases are collected and the aqueous one is extracted with additional 450 ml of ethyl acetate. The aqueous phase is discarded and the collected organic phases are washed with 750 ml of water containing NaCl. The organic phase is decolorized with 4.6 g of activated charcoal and, after 30 minute-stirring at 25° C. and subsequent filtration on Celite® layer, the filtrate is concentrated under vacuum at 50° C. until an oily residue, that is treated with 150 ml of isopropanol. The solution is concentrate under vacuum at 50° C. until a light yellow residue is obtained, which is treated with additional 150 ml of isopropanol. The suspension thus obtained is let under stirring for 30 minutes at 25° C., then for 15 hours at 0-5° C., and finally it is filtered. After washing on the filter with 2×30 ml of isopropanol, the product is dried under vacuum at 50.degree. C. to give 94 g of 1-(4-fluorophenyl)-1,3-dihydro-5-isobenzofurancarbonitrile with a 65.8% yield evaluated on the starting 5-cyanophthalide, with a purity (HPLC)=98.2-98.5% and with a 1,1-bis(4-fluorophenyl)-1,3-dihydro-5-isobenzofurancarbonitrile content lower than 0.5%.

$^1$H-NMR and $^{13}$C-NMR product data are indicated in FIG. 3.

EXAMPLE 2

Pure 1-(4-fluorophenyl)-1,3-dihydro-5-isobenzofurancarbonitrile

To a suspension of 95 g of 5-cyanophthalide in 710 ml of tetrahydrofuran, previously cooled at –10° C., 384 g of a 20% solution of 4-fluorophenylmagnesium bromide in tetrahydrofuran obtained in PREPARATION I ("Grignard solution") are dropped thereinto, in two hours, at a temperature not higher than –5° C., then, in the same conditions, in three times, 230 g, 115 g and 49 g of the same Grignard solution are dropped thereinto. At the end of addition, 675 ml of a 15% aqueous solution of ammonium chloride are added in about one hour, maintaining the temperature not higher than 0° C. The phases are separated, the aqueous one is extracted with 285 ml of tetrahydrofuran. After separation of the phases, the aqueous one is discarded and the organic phases are collected (950 ml) containing the theoretical quantity of 150 g of 3-hydroxymethyl-4-(4-fluorobenzoyl)benzonitrile, referred to the starting 5-cyanophthalide, and about 14-16% of 3-hydroxymethyl-4-[4-bis(4-fluorophenyl)hydroxymethyl]benzonitrile. The solution is cooled at 0-5° C. under nitrogen atmosphere and a solution of 23.3 g of $NaBH_4$, 230 ml of water and 1 ml of 30% NaOH is added to the mixture dropwise, in 30 minutes and at a temperature not higher than 15° C. At the end of the addition a control by HPLC (see Example 1) shows the disappearance of 3-hydroxymethyl-4-(4-fluorobenzoyl)benzonitrile. The mixture temperature is brought to 25° C. and the phases are separated; the aqueous one is eliminated and tetrahydrofuran is evaporated under vacuum at 50° C. The residue obtained is taken up with 100 ml of ethyl acetate and the solvent is evaporated under vacuum at 50° C., then it is treated with additional 350 ml of ethyl acetate. The phases are separated, the organic one is collected and the aqueous one is extracted with 230 ml of ethyl acetate. After separation of the phases, the aqueous one is discarded and the organic ones are collected obtaining 720 ml of a solution containing a theoretical quantity of 150 g of 3-hydroxymethyl-4-[(4-fluorophenyl)hydroxymethyl]benzonitrile, referred to the starting 5-cyanophthalide, and the same quantity of the by-product 3-hydroxymethyl-4-[bis(4-fluorophenyl)hydroxymethyl]benzonitrile contained in the starting solution.

To the solution thus obtained, 930 ml of 60% $H_3PO_4$ are added at 25° C. and the mixture is heated at reflux for 2 hours (81-82° C.), after which a control by HPLC (see Example 1) shows the disappearance of 3-hydroxymethyl-4-[(4-fluorophenyl)hydroxymethyl]benzonitrile and of 3-hydroxymethyl-4-[bis(4-fluorophenyl)hydroxymethyl]benzonitrile contained in the starting solution. To the mixture obtained, containing 1-(4-fluorophenyl)-1,3-dihydro-5-isobenzofurancarbonitrile and about 14-16% of 1,1-bis(4-fluorophenyl)-1,3-dihydro-5-isobenzofurancarbonitrile-, 750 ml of water are added, then the phases are separated. The organic phase is collected and the aqueous one is extracted with 600 ml of ethyl acetate, then the organic phases are collected and the aqueous one is extracted with additional 450 ml of ethyl acetate. After separation of the phases, the aqueous phase is discarded and the collected organic phases are washed with 750 ml of water containing NaCl. The separated organic phase is decolorized with 4.6 g of activated charcoal and, after 30-minute stirring at 25° C. and subsequent filtration on Celite® layer, the filtrate is concentrated under vacuum at 50° C. until an oily residue, that is treated with 50 ml of methyl-t-butylether. The mixture is concentrate under vacuum at 50° C. until a light yellow residue is obtained, which is treated with additional 50 ml of methyl-t-butylether. The suspension is stirred for 30 minutes at 25° C., then for 15 hours at 0-5° C., and finally it is filtered. It is washed with 2×30 ml of cold methyl-t-butylether and dried under vacuum at 50° C. Thus 101 g of 1-(4-fluorophenyl)-1,3-dihydro-5-isobenzofurancarbonitrile with a purity (HPLC)=98.2-98.5% and with a 1,1-bis(4-fluorophenyl)-1,3-dihydro-5-isobenzofurancarbonitrile content lower than 0.5% are obtained. The mother liquors are concentrated under vacuum at 50° C., the residue is treated with 100 ml of methyl-t-butylether and the suspension obtained is let under stirring at 25° C. for 30 minutes, then at 0-5° C. for 15 hours. After filtration, the residue is washed with 2×15 ml of methyl-t-butylether and dried under vacuum at 50° C. for 5 hours. Thus, additional 5.2 g of pure 1-(4-fluorophenyl)-1,3-dihydro-5-isobenzofurancarbonitrile are obtained. Total yield: 106.2 g=74.4% of the theoretical quantity, referred to the starting 5-cyanophthalide.

EXAMPLE 3

Citalopram Hydrobromide

To a mixture 5.42 g sodium hydride in 120 ml of dimethylsulfoxide, previously heated at 60° C. for 30 minutes, under nitrogen flow, a solution of 30 g of 1-(4-fluorophenyl)-1,3-dihydro-5-isobenzofurancarbonitrile obtained in Example 2 in 75 ml of dimethylsulfoxide is added, without exceeding 25° C. The solution is maintained under stirring for 30 minutes and, in 10 minutes, 33 g of 3-(dimethylamino)propylchloride are added without exceeding 25° C. After about 2-hour stirring at 25° C., the mixture is cooled at 10° C. and 300 ml of water are added dropwise and then 120 ml of ethyl acetate. The mixture is stirred and diluted with 1650 ml of water and 120 ml of ethyl acetate. The mixture is let 1 hour under stirring, then the phases are separated; the organic one is collected and the aqueous one is washed with 3×150 ml of ethyl acetate. After separation of the phases, the aqueous one is discarded and the collected organic ones are washed with 900 ml of water. The organic phase is dehydrated with anhydrous $Na_2SO_4$ and is concentrated under vacuum at 50° C. until an oil is obtained, which is treated with 60 ml of acetone. The mixture is stirred in order to obtain a solution, that is cooled at 10° C. and treated with about 10 ml of 48% HBr in order to adjust the pH value from 9.8-9.5 to 7.0. After 1 hour-stirring at pH=7 constant, the solvent is evaporated under vacuum at 50° C. and the residue is treated with 100 ml of acetone. The suspension is stirred at 25° C. for 30 minutes, then it is cooled at 0-5° C. and it is let at cold for 15 hours. The product is filtered, washed with cold acetone (0-5° C.) and is dried under vacuum at 50° C. Thus 34.88 g of citalopram hydrobromide with a purity (HPLC)=99.15% are obtained.

The invention claimed is:

1. A process for the preparation of pure 1-(4-fluorophenyl)-1,3-dihydro-5-isobenzofurancarbonitrile which comprises:
    (a) reacting 5-cyanophthalide with a 4-fluorophenylmagnesium halide;
    (b) treating the mixture thus obtained, containing the 3-hydroxymethyl-4-(4-fluorobenzoyl)benzonitrile and the 3-hydroxymethyl-4-[bis-(4-fluorophenyl)hydroxymethyl]benzonitrile with a reducing agent of ketones to alcohols;
    (c) submitting the mixture thus obtained, containing the 3-hydroxymethyl-4-[(4-fluorophenyl)hydroxymethyl]benzonitrile (C) and the 3-hydroxymethyl-4-[bis-(4-fluorophenyl)hydroxymethyl]benzonitrile to a cyclization reaction and isolating a mixture containing the 1-(4-fluorophenyl)-1,3-dihydro-5-isobenzofurancarbonitrile (B) and the 1,1-bis(4-fluorophenyl)-1,3-dihydro-5-isobenzofurancarbonitrile; and
    (d) treating the mixture thus obtained with a solvent capable of dissolving the 1,1-bis(4-fluorophenyl)-1,3-dihydro-5-isobenzofurancarbonitrile and in which the 1-(4-fluorophenyl)-1,3-dihydro-5-isobenzofurancarbonitrile (B) is insoluble and recovering the pure 1-(4-fluorophenyl)-1,3-dihydro-5-isobenzofurancarbonitrile (B), wherein said solvent is isopropanol or methyl-t-butylether.

2. A process according to claim 1, wherein, in step (b) the reduction is carried out with $NaBH_4$ in water and sodium hydroxide.

3. A process according to claim 1, wherein, in step (c), the cyclization is carried out with phosphoric acid in a biphasic water/organic solvent medium.

4. A process according to claim 3, wherein said biphasic medium consists of water/ethyl acetate.

5. A process according to any one of claims 1 to 4, wherein, in step (d), isopropanol or methyl-t-butylether is used as a solvent capable of dissolving the 1,1-bis(4-fluorophenyl)-1,3-dihydro-5-isobenzofurancarbonitrile and in which the 1-(4-fluorophenyl)-1,3-dihydro-5-isobenzofurancarbonitrile (B) is insoluble.

6. A process according to any one of claims 1 to 5, wherein the 1-(4-fluorophenyl)-1,3-dihydro-5-isobenzofurancarbonitrile (B) is further reacted with a 3-(dimetylamino)propyl halide in the presence of a basic condensing agent and citalopram is isolated as free base or as a pharmaceutically acceptable salt thereof.

7. A process according to claim 6, wherein the chloride is used as an halide, sodium hydride is used as a basic condensing agent and the condensation is carried out in dimethylsulfoxide.

8. A process for the preparation of citalopram or of a pharmaceutically acceptable salt thereof, which comprises:
    (a) reacting 5-cyanophthalide with a 4-fluorophenylmagnesium halide;
    (b) treating the mixture thus obtained, containing the 3-hydroxymethyl-4-(4-fluorobenzoyl)benzonitrile and the 3-hydroxymethyl-4-[bis-(4fluorophenyl)hydroxymethyl]benzonitrile with a reducing agent of ketones to alcohols;
    (c) submitting the mixture thus obtained, containing the 3-hydroxymethyl-4-[(4-fluorophenyl)hydroxymethyl]benzonitrile (C) and the 3-hydroxymethyl-4-[bis-(4-fluorophenyl)hydroxymethyl]benzonitrile to a cyclization reaction and isolating a mixture containing the 1-(4-fluorophenyl)-1,3-dihydro-5-isobenzofurancarbonitrile (B) and the 1,1-bis(4-fluorophenyl)-1,3-dihydro-5-isobenzofurancarbonitrile;
    (d) treating the mixture thus obtained with a solvent capable of dissolving the 1,1-bis(4-fluorophenyl)-1,3-dihydro-5-isobenzofurancarbonitrile and in which the 1-(4-fluorophenyl)-1,3-dihydro-5-isobenzofurancarbonitrile (B) is insoluble and recovering the pure 1-(4-fluorophenyl)-1,3-dihydro-5-isobenzofurancarbonitrile (B), wherein said solvent is isopropanol or methyl-t-butylether;
    (e) treating the pure 1-(4-fluorophenyl)-1,3-dihydro-5-isobenzofurancarbonitrile (B) with a 3-(dimethylamino) propyl halide in the presence of a basic condensing agent and isolating citalopram as free base or as a pharmaceutically acceptable salt thereof.

9. A process according to claim 8, wherein, in step (b) the reduction is carried out with $NaBH_4$ in water and sodium hydroxide.

10. A process according to claim 8, wherein, in step (c), the cyclization is carried out with phosphoric acid in a biphasic water/organic solvent medium.

11. A process according to claim 10, wherein said biphasic medium consists of water/ethyl acetate.

12. A process according to any one of claims 8 to 11, wherein, in step (d), isopropanol or methyl-t-butylether is used as a solvent capable of dissolving the 1,1-bis(4-fluorophenyl)-1,3-dihydro-5-isobenzofurancarbonitrile and in which the 1-(4fluorophenyl)-1,3-dihydro-5-isobenzofurancarbonitrile (B) is insoluble.

* * * * *